United States Patent [19]

Cavazza et al.

[11] Patent Number: 4,551,477
[45] Date of Patent: Nov. 5, 1985

[54] ESTERS OF ALKOXY-ACYLDERIVATIVES OF CARNITINE AND PHARMACEUTICAL COMPOSITIONS CONTAINING SAME

[75] Inventors: Claudio Cavazza; Maria O. Tinti, both of Rome, Italy

[73] Assignee: Sigma-Tau Industrie Farmaceutiche Riunite S.P.A., Rome, Italy

[21] Appl. No.: 625,715

[22] Filed: Jun. 28, 1974

Related U.S. Application Data

[63] Continuation of Ser. No. 263,655, May 14, 1981, abandoned.

[30] Foreign Application Priority Data

May 30, 1980 [IT] Italy ................................ 48853 A/80

[51] Int. Cl.⁴ ..................... C07C 101/18; A61K 31/22
[52] U.S. Cl. ..................................... 514/547; 560/170
[58] Field of Search ......................... 560/170; 424/311

[56] References Cited

U.S. PATENT DOCUMENTS

3,922,340 11/1975 Mewa ................................... 424/319
4,194,006 3/1980 Cavazza .............................. 424/319
4,237,167 12/1980 Cavazza .............................. 424/319

OTHER PUBLICATIONS

Wilson, "Textbook of Organic Medical and Pharmaceutical Chemistry," pp. 39-40 (1954).

Primary Examiner—Michael L. Shippen
Attorney, Agent, or Firm—Ladas & Parry

[57] ABSTRACT

A novel class of esters of alkoxy-acylderivatives of carnitine, wherein the alkoxy-acyl radical has from 3 to 6 carbon atoms (typically: methoxyacetyl, methoxypropionyl, ethoxyacetyl, ethoxypropionyl and propoxyacetyl) is prepared by esterifying carnitine and then acylating the carnitine ester. Such esters are therapeutically useful in the treatment of cardiac disorders, hyperlipidaemias and hyperlipoproteinaemias.

3 Claims, No Drawings

ESTERS OF ALKOXY-ACYLDERIVATIVES OF CARNITINE AND PHARMACEUTICAL COMPOSITIONS CONTAINING SAME

This is a continuation of co-pending application Ser. No. 263,655 filed on May 14, 1981 now abandoned.

The present invention relates to a novel class of esters of alkoxy-acylderivatives of carnitine, the process for their preparation, the pharmaceutical compositions containing such esters and their use in therapy.

More particularly, the present invention relates to esters of alkoxy-acylderivatives of carnitine having general formula (I):

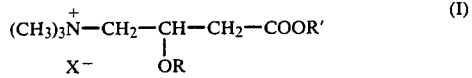

wherein:
- $X^-$ is an halogen anion selected between chlorine and bromine, preferably chlorine;
- R is a alkoxy-acyl radical having from 3 to 6 carbon atoms, such radical being preferably selected from the group consisting of methoxyacetyl, 2- and 3- methoxypropionyl, ethoxyacetyl, 2- and 3- ethoxypropionyl and propoxyacetyl;
- R' is an alkyl radical having from 1 to 6 carbon atoms, such radical being preferably selected from the group consisting of methyl, ethyl, propyl, isopropyl, butyl and isobutyl.

It should be understood that the foregoing general formula (I) encompasses the esters of the present invention both in their optically active forms and in their racemic form.

It has been found that the compounds of the present invention possess valuable pharmacological properties and can, therefore, be utilized in the therapeutical field.

More particularly: The esters of formula (I) showed to be endowed with a prolonged and effective inotropic action and devoid of any effects depressing the myocardial excitability. Although no theoretical interpretation is intended here, it is deemed that the foregoing is due to the capability of the ester bond of protecting acyl-carnitine against rapid metabolic degradation and sharp fall of blood levels thereof.

Moreover, the esters of formula (I) have shown to be endowed with an antifibrillation effect.

The direct antiarrhythmic effect of the quinidine type is complemented by the adrenaline-antagonizing activity.

The esters of formula (I) have been shown to restore the α- and β-lipoprotein ratio to normal.

The compounds of this invention can, therefore, be therapeutically utilized (a) in cases of myocardial hypocontractility, such as in cardiogenic shock provoked by primary absence of contractile force;

(b) for the treatment of functional arrhythmias and arrhythmias secondary to myocardial-sclerotic processes; and (c) for the treatment of hyperlipidaemias and hyperlipoproteinaemias.

The process for preparing the esters of alkoxy-acylderivatives of carnitine in accordance with the present invention comprises the steps of:

(a) esterifying carnitine by suspending carnitine in an alcohol having formula R'OH wherein R' has the previously specified meaning, bubbling into the resulting suspension gaseous hydrochloric acid till complete dissolution of carnitine, refluxing the resulting solution and isolating the carnitine ester by concentration and neutralization of said solution; and (b) acylating the carnitine ester of step (a) by reacting it with an excess of acyl halogenide of formula RX wherein R has the previously specified meaning and X is an halogen atom selected between chlorine and bromine, keeping the resulting reaction mixture for about 42–80 hours at about 35°–60° C. and isolating the ester of alkoxy-acyl carnitine of formula (I) by means of conventional procedures.

In step (b) the carnitine ester of step (a) can be dissolved in an inert, anhydrous organic solvent and the reaction mixture be kept in a stream of inert, anhydrous gas. Alternatively, the carnitine ester of step (a) can be reacted with an excess of acylating agent in the absence of solvent and the reaction mixture be kept in a moisture-free environment.

In case the carnitine ester is dissolved in a solvent, the solvent is preferably selected among acetone, methylene chloride, chloroform and acetonitrile.

As mentioned, the carnitine ester is reacted with an excess of an acylating agent. Preferably, the molar ratio between the carnitine ester and the acylating agent is comprised between 1:2 and 1:4.

The following non limiting examples aim at illustrating the preparation of some esters of alkoxy-acylderivatives of carnitine in accordance with the present invention.

EXAMPLE 1

Preparation of methoxyacetyl carnitine isobutyl ester (1) Preparation of carnitine isobutyl ester: Carnitine hydrochloride (10 g; 0.05 moles) was suspended in 100 ml of isobutanol. The resulting mixture was cooled with an ice bath and gaseous hydrochloric acid was bubbled therein till complete saturation. The resulting mixture was kept under reflux conditions for 2 hours. The mixture was then concentrated and subsequently taken up with isobutanol and neutralized with Amberlist 21. The resulting solution was then filtered and brought to dryness. 12 g of carnitine isobutyl ester were obtained.

(2) Preparation of methoxy-acetyl chloride: $SOCl_2$ (1.1 cc; 0.0125 moles) was added to methoxy-acetic acid (1.08 g; 0.012 moles). The resulting reaction mixture was kept at room temperature for 12 hours and was then washed three times with a mixture of chloroform anhydrous ethyl ether and subsequently concentrated under vacuum (P=80 mm Hg) at 30° C. 1.2 g of methoxy-acetyl chloride were obtained.

(3) Reaction between carnitine isobutyl ester and methoxy-acetyl chloride: Carnitine isobutyl ester (1.1 g; 0.0043 moles) prepared as indicated in step (1) was dissolved in anhydrous acetone and to the resulting solution the methoxy-acetyl chloride (970 mg; 0.009 moles) which had been prepared as indicated in step (2) was added. The reaction mixture was brought to dryness and the residue kept in an atmosphere of inert gas (nitrogen and argon) at 40° C. for 48 hours. Subsequently, the residue was crystallized from isopropanol-ethyl ether.

The title product was obtained with a yield of 55%. TLC Eluant: $CHCl_3$, MeOH, $CH_3COONa$ 0.01M 40,40,10.

NMR D$_2$O δ  5.8 (1H, m, —C$\underline{H}$—  );
                    |
                    OCOCH$_2$OCH$_3$ 4.2 (2H, s, —COOCH$_2$—);

3.9 (4H, m, $\diagdown \!\!\!\!\!\!+\!\!\!\!\!\!\diagup$NCH$_2$—, —C$\underline{H_2}$OCH$_3$);

3.4 (3H, s, —OCH$_3$);

3.2 (9H, s, —$\overset{+}{N}$—(CH$_3$)$_3$);

2.9 (2H, d, —CH$_2$COO);

1.9 (1H, m, C$\underline{H}$$\diagup^{CH_3}_{\diagdown CH_3}$);

0.96 (6H, d, —CH$\diagup^{\underline{CH_3}}_{\diagdown \underline{CH_3}}$)

EXAMPLE 2

Preparation of ethoxyacetyl carnitine isobutyl ester (1) Preparation of carnitine isobutyl ester: Carnitine hydrochloride (10 g; 0.05 moles) was suspended in 100 ml of isobutanol. The resulting suspension was cooled with an ice bath and gaseous hydrochloric acid was bubbled therein till complete saturation. The resulting mixture was kept under reflux conditions for 2 hours. The mixture was concentrated in order to remove the alcohol; the concentrate was dissolved in distilled water and neutralized with IR 45 resin. The resulting product was lyophilized, thus obtaining 12 g of carnitine isobutyl ester.

(2) Preparation of ethoxy acetyl chloride: To ethoxy acetic acid (1.3 cc; 0.012 moles) thionyl chloride (1.1 cc; 0.0125 moles) was added. The resulting mixture was kept at room temperature for 12 hours. The reaction mixture was washed three times with a mixture of chloroform-anhydrous ethyl ether and subsequently concentrated under vacuum (80 mm Hg) at 30° C. 1.15 g of ethoxy acetyl chloride were obtained.

(3) Reaction between carnitine isobutyl ester and ethoxy acetyl chloride: Carnitine isobutyl ester (1.1 g; 0.043 moles) was dissolved in anhydrous acetone and to the resulting solution ethoxy acetyl chloride (1.15 g; 0.009 moles) was added. The reaction mixture was brought to dryness and the residue kept in an atmosphere of inert gas (argon) at room temperature for 2 days.

Subsequently, the residue was crystallized from isopropanol-ethyl ether. The title product was obtained with a yield of 65%.

| TLC Eluant: | CHCl$_3$ | 40 |
| | CH$_3$OH | 40 |
| | CH$_3$COONa | 0.01M 10 |
| NMR | D$_2$O δ 5.8 (1H, m, CH ); | |
| |                        |             | |
| |                        OCO | |
| | 4.2 (2H, s, —COCH$_2$O—); | |
| | 4.0 (4H, m, —COOCH$_2$—, O—C$\underline{H_2}$CH$_3$); | |

3.7 (2H, d, $\diagdown \!\!\!\!\!\!+\!\!\!\!\!\!\diagup$N CH$_2$—); 3.3 (9H, s, CH$_3$—$\overset{+}{\underset{CH_3}{N}}\!\!\!\diagdown$—);
$\diagup$CH$_3$ 2.7 (2H, d, —CH$_2$COO—);

1.9 (1H, m, C$\underline{H}$$\diagup^{CH_3}_{\diagdown CH_3}$);

1.6 (3H, t, —CH$_2$C$\underline{H_3}$); 1.1 (6H, d, —CH$\diagup^{\underline{CH_3}}_{\diagdown \underline{CH_3}}$).

EXAMPLE 3

Preparation of 3-ethoxypropionyl carnitine isopropyl ester (1) Preparation of carnitine isopropyl ester: Carnitine hydrochloride (10 g; 0.05 moles) was suspended in 100 cc of isopropanol. The resulting suspension was cooled with ice bath and gaseous hydrocloric acid was bubbled therein till complete saturation. Subsequently the mixture was heated under reflux conditions for 2 hours. The mixture was then concentrated, subsequently taken up with isopropanol and neutralized with Amberlist 21. The resulting solution was filtered and brought to dryness. 11 g of carnitine isopropyl ester were obtained.

(2) Preparation of 3-ethoxy propionyl chloride: To 3-ethoxy propionic acid (1.18 g; 0.01 moles) oxalyl chloride (3.78 g; 0.03 moles) was added. The resulting mixture was kept under stirring at room temperature for 4 hours. Subsequently, the resulting mixture was washed three time with anhydrous ethyl ether and concentrated under vacuum (P=90 mmHg) at 40° C. 1.2 g of 3-ethoxy propionyl chloride were obtained.

(3) Reaction between carnitine isopropyl ester and 3-ethoxy propionyl chloride: Carnitine isopropyl ester (1.1 g; 0.0045 moles) obtained in the previous step (1) was dissolved in anhydrous methylene chloride and to the resulting solution 3-ethoxy propionyl chloride (1.2 g; 0.009 moles) obtained in the previous step (2) was added. An inert gas (nitrogen) was bubbled into the reaction mixture till complete evaporation of the solvent. Subsequently, the mixture was kept at 40° C. for 24 hours. The residue was crystallized from isopropanol-aceton-ether. The product was obtained with a yield of 60%. TLC Eluant: chloroform, methanol, sodium acetate 0.01M 40/40/10

NMR D$_2$O δ  5.7 (1H, m, —C$\underline{H}$—  );
                    |
                    OCOCH$_2$ 5.0 (1H, m, —COOCH—);

4.0–3.5 (6H, m, C$\underline{H_2}$OC$\underline{H_2}$—, $\diagdown \!\!\!\!\!\!+\!\!\!\!\!\!\diagup$N—CH$_2$);

3.3 (9H, s, $\overset{+}{N}$—(CH$_3$)$_3$);

2.9 (2H, d, —CH—C$\underline{H_2}$COO);

2.5 (2H, t, —OCOC$\underline{H_2}$CH$_2$—);

1.4–1.2 (9H, m, —CH$_2$CH$_3$, —CH(CH$_3$)$_2$).

1.2 (6H, d, —CH(CH$_3$)$_2$).

EXAMPLE 4

Preparation of 2-methoxy propionyl carnitine isopropyl ester

Preparation of the 2-methoxy propionic acid: 2-bromo propionic acid (30.4 g; 0.2 moles) was added to a solution of 10 g of metal sodium in 150 ml of anhydrous methanol. The resulting mixture was kept under stirring at 60° C. for 3 days. Subsequently, the solution was concentrated under vacuum, the residue was taken up with water, acidified with conc. HCl and the resulting aqueous solution was extracted with ethyl ether. The organic phase, washed with water and dried on Na$_2$SO$_4$, was concentrated under vacuum. Pure 2-methoxy propionic acid was thus obtained, as confirmed by NMR analysis.

(2) Preparation of 2-methoxy propionyl chloride: 2-methoxy propionic acid (3.128 g; 0.03 moles) and thionyl chloride (2.3 g; 0.04 moles) were kept under stirring at 50° C. for 4 hours in anhydrous environment. The excess of thionyl chloride was removed under vacuum and the raw material thus obtained was utilized in the subsequent reaction.

(3) Preparation of 2-methoxy propionyl carnitine isopropyl ester: Carnitine isopropyl ester (2.4 g; 0.01 moles) prepared as previously described and 2-methoxy propionyl chloride were reacted at 50° C. for 3 days. The reaction mixture was treated with ethyl ether, the raw material which precipitated was taken up with acetonitrile and decolorized with activated carbon.

To the acetonitrile solution ethyl ether was added, thus obtaining a precipitate which, upon examination with HPLC (column C$_{18}$: eluant NH$_4$H$_2$PO$_4$—CH$_3$CN 85-15, flow rate 1 ml/min. RI detector) turned out to consist of the product mixture. The mixture was purified with preparative HPLC: CHROMATOSPAS PREP 100, column pressure 6 Barr; eluant pressure 5 Barr; flow rate 15 ml/min; lichroprep RP8 resin, diameter 3.60μ. The product thus obtained was shown to consist of 2-methoxy propionyl carnitine isopropyl ester. Yield 50%.

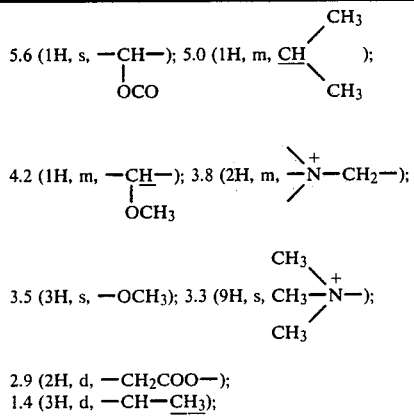

NMR D$_2$O δ

5.6 (1H, s, —CH(OCO)—); 5.0 (1H, m, CH(CH$_3$)$_2$);

4.2 (1H, m, —CH(OCH$_3$)—); 3.8 (2H, m, \+N—CH$_2$—);

3.5 (3H, s, —OCH$_3$); 3.3 (9H, s, CH$_3$—\+N(CH$_3$)—);

2.9 (2H, d, —CH$_2$COO—);
1.4 (3H, d, —CH—CH$_3$);

PHARMACOLOGICAL ACTIVITIES

The pharmacological properties of the compounds of the present invention were investigated with the following techniques:

(a) Acute toxicity (LD50)

Acute toxicity was investigated by using the method disclosed by Weil C. S. in "Tables for convenient calculation of median-effective dose (LD50 or ED50) and instructions in their use", Biometrics, 249–253, 1952.

The tolerance of the compounds under examination was investigated in mice after administration by the intraperitoneal or oral route. The obtained results show that the compounds exhibit excellent tolerance. (see the Table).

(b) Inotropic effect

Rabbit hearts isolated by the Langendorff method were perfused with oxygenized Ringer solution at 38.2° C. The isometric contractions, electrogardiogram and coronary flow were recorded using a "Battaglia-Rangoni" polygraph. By removing the oxygen from the perfusion fluid, metabolic damage was induced in the cardiac muscle, up to an 80% reduction in the cardiac contractile force.

Under these conditions of prolonged anoxia the aerobic glycolysis of the myocardium is slowed down, accompanied by the storage of acid catabolites due to both the accumulation of pyruvic acid and its conversion to lactic acid which cannot be utilized because of the depression of pyridine enzymes, such as LDH (lactodehydrogenase). This has repercussions on the anaerobic glycolysis affecting an ever increasing number of enzymes, accompanied by a progressive and increasingly critical exhaustion of the myocardium. Thus a whole series of cardiac muscle fatigue levels occurs which can be observed by the behavior of the examined parameters, namely the contractile force, coronary flow, heart rate and cardiac rhythm. As soon as the contractile force was reduced by 80%, the perfusion fluid was once again oxygenized either without adding other compounds (controls) or with the addition of the compounds under examination.

The contractile force of the heart was examined, which shows a positive inotropic effect after 10 minutes from the interruption of the anoxic period (myocardial restoration). The results, evaluated by means of Student's "t" test, show that the compounds under examination induce a positive inotropic effect statistically significant against the controls.

In the Table there are shown the percentage value of increase against the controls.

(c) Antiarrhythmic effect

In order to evaluate the antiarrhythmic activity of the carnitine derivatives of this invention studied with in vivo tests in addition to and in comparison with the currently employed in vitro tests, the method disclosed by Nwangwu et al. (Arch. Int. Pharmacodyn., 1977, 229, 219) was used.

According to this method an aconitine solution is injected into the caudal vein of mice and the onset time of arrhythmia and tachycardia after 2 to 60 minutes from administration of the compounds under examination is recorded.

The antiarrhythmic activity calculated from the increase in the latency time of the onset of the arrhythmias of the treated animals in comparison with the controls, is illustrated in the Table.

(d) Adrenaline-antagonizing effect

Groups of ten male Albino Swiss mice, weighing 12–22 g, were intraperitoneally administered either with the esters of the present invention or with saline (control) and, after 30 minutes, with adrenaline (treated) at a dose capable of bringing about death to 100% of the control animals due to ventricular fibrillation and cardiac lesions ensuing from increase in frequency, pressure and oxygen uptake from the myocardium.

Mortality was checked for 36 hours and the effect of the compounds expressed as percentage of surviving animals, is shown in the Table.

Should it be deemed necessary, larger doses can be administered, in view of the low toxicity of the compounds of this invention.

Non-limiting example of dosages are as follows:
fials: 5–500 mg
capsules: 15–50 mg
tablets: 15–500 mg
oral solutions: 15–50 mg

What is claimed is:

1. An ester of alkoxy-carboxyl derivatives of carnitine having general formula (I):

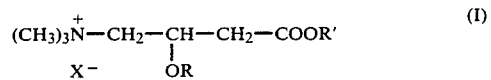

wherein:
- $X^-$ is a halogen anion selected from chlorine and bromine;
- R is an alkoxy-substituted alkanoyl group radical having from 3 to 6 carbon atoms; and
- R' is an alkyl radical having from 1 to 6 carbon atoms.

2. An ester according to claim 1, wherein said radical R is selected from the group consisting of methoxya-

TABLE

Pharmacological activity of some esters of alkoxy-acyl derivatives of carnitine.
$LD_{50}$ by the intraperitoneal route in mice, antifibrillatory activity in mice, adrenaline-antagonizing activity in mice, inotropic activity on rabbit isolated heart.

| $(CH_3)_3\overset{+}{N}-CH_2-\underset{OR}{CH}-CH_2-COOR'$ | | $LD_{50}$ mg kg$^{-1}$ i.p. | Antifibrillatory activity (dose mg kg$^{-1}$ i.v.) % reduction | Antiadrenaline activity (dose mg kg$^{-1}$ i.p.) % mortality reduction | Inotropic effect (dose $10^{-5}$ gl$^{-1}$) % of controls |
|---|---|---|---|---|---|
| R = methoxyacetyl; | R' = methyl | 1200 | 75 (300) | 70 (450) | +72 |
| | R' = ethyl | 550 | 70 (50) | 70 (70) | +58 |
| | R' = propyl | 650 | 100 (50) | 75 (50) | +78 |
| | R' = isopropyl | 800 | 80 (50) | 75 (50) | +55 |
| | R' = butyl | 550 | 75 (40) | 70 (100) | +55 |
| | R' = isobutyl | 690 | 85 (75) | 60 (300) | +79 |
| R = ethoxyacetyl; | R' = methyl | 1100 | 90 (150) | 75 (300) | +55 |
| | R' = ethyl | 600 | 65 (35) | 50 (50) | +68 |
| | R' = propyl | 620 | 75 (50) | 75 (100) | +49 |
| | R' = isopropyl | 700 | 70 (50) | 60 (100) | +72 |
| | R' = butyl | 600 | 75 (40) | 75 (100) | +58 |
| | R' = isobutyl | 750 | 70 (10) | 50 (70) | +70 |
| R = 2-ethoxypropionyl; | R' = isopropyl | 1200 | 70 (50) | 50 (300) | +50 |
| R = 2-methoxypropionyl; | R' = isopropyl | 850 | 68 (50) | 58 (100) | +70 |

The compounds of the present invention are administered either orally or parenterally, in any of the usual pharmaceutical forms which are prepared by conventional procedures, well known to the experts in the pharmaceutical field. These forms comprise solid and liquid oral unit dosage forms, such as tablets, capsules, solutions, syrups and the like and injectable forms such as sterile solutions for ampoules and vials.

For preparing such pharmaceutical forms the usual solvents, diluents and excipients are used. Optionally, preservative, sweetening and flavoring agents can also be present. Non limiting examples of such substances are sodium carboxymethyl cellulose, polysorbate, mannitol, sorbitol, starch, avicel, talc and other substances which will be apparent to the experts of pharmaceutical techniques.

The dose to be administered will be determined by the attending physician taking the age, weight and general conditions of the patient into account, utilizing sound professional judgment. Although effective results can be observed even at doses as low as from 5 to 8 mg/kg of body weight daily, a daily dose of from about 10 to about 50 mg/kg of body weight is preferred.

cetyl, 2- and 3-methoxypropionyl, ethoxyacetyl, 2- and 3-ethoxypropionyl and propoxyacetyl, and said alkyl radical R' is selected from the group consisting of methyl, ethyl, propyl, isopropyl, butyl and isobutyl.

3. A pharmaceutical composition for the treatment of cardiac disorders, hyperlipoproteinaemias, or hyperlipidaemias, comprising a therapeutically effective amount of an ester of carnitine of formula (I)

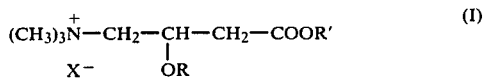

wherein:
- $X^-$ is a halogen anion selected from chlorine and bromine;
- R is an alkoxy-substituted alkanoyl radical having from 3–6 carbon atoms; and
- R' is an alkyl radical having from 1 to 6 carbon atoms, and a pharmacologically acceptable excipient.

* * * * *

UNITED STATES PATENT AND TRADEMARK OFFICE
CERTIFICATE OF CORRECTION

PATENT NO. : 4,551,477
DATED : November 5, 1985
INVENTOR(S) : Claudio CAVAZZA

It is certified that error appears in the above-identified patent and that said Letters Patent is hereby corrected as shown below:

Filing date, item [22], delete "June 28, 1974" and replace therefor:

--June 28, 1984--

Signed and Sealed this

First Day of April 1986

[SEAL]

*Attest:*

DONALD J. QUIGG

*Attesting Officer*  *Commissioner of Patents and Trademarks*